United States Patent
Frenkel et al.

(10) Patent No.: US 6,352,630 B1
(45) Date of Patent: Mar. 5, 2002

(54) ELECTROCHEMICAL SYSTEM FOR DETERMINING BLOOD COAGULATION TIME

(75) Inventors: Erik Jan Frenkel, Neuchâtel; André Haeberli, Gümligen; Anita Moresi, Bern, all of (CH)

(73) Assignee: Asulab S.A., Bienne (CH)

( * ) Notice: Subject to any disclaimer, the term of this patent is extended or adjusted under 35 U.S.C. 154(b) by 0 days.

(21) Appl. No.: 09/499,358

(22) Filed: Feb. 8, 2000

(30) Foreign Application Priority Data

Feb. 23, 1999 (EP) .............................................. 99103418

(51) Int. Cl.$^7$ ......................... G01N 27/327; C12Q 1/56
(52) U.S. Cl. ............................ 204/403; 435/13; 422/73
(58) Field of Search ........................... 435/13; 422/73; 204/403; 205/775

(56) References Cited

U.S. PATENT DOCUMENTS

| | | | |
|---|---|---|---|
| 4,304,853 A | | 12/1981 | Jozenfonvicz et al. |
| 5,378,628 A | * | 1/1995 | Gratzel et al. .............. 435/288 |
| 5,418,141 A | | 5/1995 | Zweig et al. |
| 5,762,770 A | * | 6/1998 | Pritchard et al. ........... 204/403 |
| 6,066,243 A | * | 5/2000 | Anderson et al. ........... 204/403 |
| 6,168,699 B1 | * | 1/2001 | Frenkel et al. .............. 204/400 |

FOREIGN PATENT DOCUMENTS

| | | | |
|---|---|---|---|
| EP | 737 853 | | 10/1996 |
| WO | 07492 | * | 4/1993 |
| WO | 94/16095 | | 7/1994 |

OTHER PUBLICATIONS

Peuriot et al., "Electrochemical activity determination of trypsin–like enzymes II–Thrombin", Thombosis Research, vol. 19, pp. 647–654, month N/A, 1980.*

Peuriot et al., "Electrochemical activity determination of trypsin–like enzymes III", Thrombosis Research, vol. 20, pp. 299–306, month N/A, 1980.*

Peuriot et al., "Electrochemical activity determinations of trypsin–like enzymes IV", Thrombosis Research, vol. 22, pp. 303–308, month N/A, 1981.*

Peuriot et al., "The electrochemical activity determination of trypsin–like enzymes", J. Electrochem. Soc., vol. 123, pp. 1233–1238, Jun. 1981.*

* cited by examiner

*Primary Examiner*—Robert J. Warden, Sr.
*Assistant Examiner*—Koj K. Olsen
(74) *Attorney, Agent, or Firm*—Sughrue Mion, PLLC

(57) ABSTRACT

Electrochemical system for measuring a value representing the coagulation time of a drop of whole blood including:

an electrochemical sensor in the shape of a strip of small dimensions bearing at least a reference electrode and a working electrode on which a specific reagent is immobilized, including at least one chemical substrate one terminal link of which can be cut off by the thrombin enzyme to give charged groups (LG), and a measuring apparatus intended to receive said sensor allowing a given voltage or current to be imposed across the electrodes of the sensor, the electric signal resulting from the migration of the charged groups to be processed, said signal to be correlated with a value representing the coagulation time, and said value to be displayed on a display panel.

The specific reagent preferably includes an oligopeptidic derivative as a substrate, a thromboplastin and a buffer medium.

15 Claims, 4 Drawing Sheets

ELECTROCHEMICAL SYSTEM FOR DETERMINING BLOOD COAGULATION TIME

BACKGROUND OF THE INVENTION

The present invention concerns an individual system for determining whole blood coagulation time, a disposable sensor of small dimensions including a specific thrombin enzyme reagent allowing an electrochemical determination and an electronic measuring apparatus allowing an electric signal received from said sensor to be correlated when it has been introduced into the apparatus and a drop of the blood to be analysed has been deposited thereon.

The invention concerns more particularly a measuring apparatus and sensor of this type allowing the prothrombin time (PT) to be determined by amperometry when the reagent composition deposited on the sensor includes a chemical substrate of which a terminal fraction can be selectively cut off by the thrombin enzyme by releasing a charged group.

Checking the blood coagulation time, i.e. the aptitude of the blood constituents to form a clot to prevent the risk of haemorrhage, forms part of the routine examinations, or even daily examinations, performed in numerous acquired pathological, traumatic or postoperative situations. It is for example necessary during treatment with anticoagulants in the case of heart related diseases to be able to adjust the dosage of the medicine accurately, for example warfarin or heparine, in order to avoid the risk of haemorrhages in the event of an overdose or conversely, the risk of thrombosis if the quantity of anticoagulant administered is insufficient.

Different parameters have been retained for performing this determination, but the most common is measuring the prothrombin time (PT) after activation, i.e. the period of time after which the formation of a clot is observed with a blood sample taken from the patient. Such analyses were for a long time entirely dependent upon the expertise of specialised laboratory personnel equipped with complex and cumbersome apparatus. This had the drawback of obliging the patient to travel, requiring preparation of a blood sample taken at home, for example by adding citrate, to wait until a laboratory analysis could be performed.

Progress made as regards miniaturisation, in particular using electronic components, has, for slightly more than ten years or so, enabled the patient to have various types of more compact equipment allowing him to perform a coagulation time measurement at home. Most of these individual pieces of equipment rely on the same principles as laboratory apparatus, namely direct observation of the erythrocyte dynamics in a blood sample, to which the usual coagulation reagents have been added, when it changes from a fluid state to a viscous or clotted state.

According to a first principle, the period of time after which a prepared blood sample no longer flows through a capillary tube, or through the calibrated choke of a tube of larger diameter, supported by single use receiving means which can be fitted to a measuring apparatus, is measured. This flow is generally forced by means of a pneumatic pump device integrated in the measuring apparatus, and the period of time after which coagulation occurs is generally detected by optical means. Devices of this type are for example disclosed in U.S. Pat. Nos. 3,486,859, 3,890,098 and 5,302,348. An apparatus relying on this principle is for example that proposed under the trademark <<Hemochron>> or according to a more recent variant under the trademark <<Protime Microcoagulation System>> by International Technidyne Corporation (NJ-USA). The measuring apparatus obviously includes a power source for supplying power both to the mechanical part (pump) and the end of coagulation check (optical detection). It will further be observed that each receiving means for the blood sample to be analysed, which is disposable after the first use is relatively cumbersome (approximately 3×9 cm) and depends upon a precision technology (calibration of the capillary tube or the choke) which necessarily contributes towards increasing the cost of each analysis performed.

According to a second principle, one measures the period of time after which a prepared blood sample, deposited in a disposable cupel allows the immobilisation by coagulation of a magnetic object moved by a rotating magnetic field, the detection of the coagulation phenomenon being again most often performed by optical means. U.S. Pat. No. 3,967,934 already discloses this principle wherein the container intended to receive the sample contains a ferromagnetic ball. Such as device is for example used in the apparatus distributed by Nycomed Pharma (Oslo, Norway) under the trademark <<Thrombotrack>>. According to another variant, described for example in U.S. Pat. No. 5,154,082, the ball is replaced by ferromagnetic particles, which are also subjected to an electromagnetic field. This has enabled a reagent to be made in a dry form, deposited on a support, the mobility of the erythrocytes still being detected by optical means. A device of the preceding type corresponds for example to a Boehringer Mannheim (Germany) apparatus sold under the trademark Coaguchek. The products proposed corresponding to this second principle have the same drawbacks as those already mentioned for the apparatus according to the first principle with the exception perhaps of the lower cost of the blood sample receiving means for the Coaguchek apparatus.

Comparative tests performed with the methods and devices of the aforecited prior art (<<Home Prothrombin Estimation>> by Angelida Bernado et al., Thrombosis, Embolism and Bleeding, ch. 3.5—E.g. Butchart and E. Bodnar ICR Publishers 1992) have demonstrated that the medical follow-up of a patient at home was at least as satisfactory as that of a patient in a hospital environment, but that reliable and reproducible results could not be obtained unless the patient had had a reasonable period of training. The apparatus of the prior art are of course provided for domestic use, can easily be moved but yet remain relatively too voluminous for a patient to be able to keep at home about his person, for example in a pocket, while he moves around. It is doubtless also desirable, for the reliability of the measurements which depend upon devices which are both optical and electromechanical, for said apparatus to be moved as little as possible.

It will be observed finally that, according to one or other of the above principles, the electric power source necessary for supplying power to the optical and electromechanical devices must be relatively large when it is autonomous (battery) but that it is never directly involved in the coagulation time measurement.

Reference can however be made to a U.S. Pat. No. 3,674,014 of 1972 which discloses a syringe whose inner wall includes a succession of electrodes allowing the variation in impedance of the analyte to be measured, by means of an oscilloscope connected to said syringe, progressively as the coagulation phenomenon occurs. Such a device still only relies on the variation in the properties of the analyte during coagulation and is evidently not intended for individual use.

The device disclosed in European Patent No. EP 0 679 193, allowing inter alia, the prothrombin time to be measured, includes two electrodes which are only involved in said determination to detect, from a signal representing the resistance variation between the electrodes, the presence of a blood sample on the receiving means, and have no direct role in measuring a period of time. In this device, the period of time measurement is performed by a photometric determination of the fluorescence of the medium from an oligopeptidic substrate having Rhodamine as its leaving group able to be released by being cut off by the thrombin enzyme. A substrate of this type is for example disclosed in U.S. Pat. No. 4,557,862. A colorimetric method using a slightly different substrate, having p-nitroaniline as chromatophore, corresponds for example to the product marketed by Nycomed Pharma under the trademark <<NYCOTEST-CHROM>>.

These calorimetric methods have the advantage of no longer relying on mechanical or electromechanical means, but, on the other hand, they require an additional centrifugation or ultrafiltration step through a membrane, as proposed in European Patent No. EP 0 679 193, to remove the erythrocytes in order to perform detection on the plasmatic part alone. These methods have the additional drawback of requiring a measuring apparatus having high precision optical detection means, thus a relatively fragile apparatus which is difficult to transport, and requiring a relatively long colour development time, generally longer than 5 minutes, before the measurement can be performed.

A method with a simpler principle, which relies on an electrochemical measurement, is disclosed in U.S. Pat. No. 4,304,853. This method consists in introducing into a measuring cell including at least two electrodes, a citrated blood sample and an oligopeptidic substrate which has to be kept in a solvent medium such as dimethylsulfoxide (DMSO). The substrate is formed of a chain of amino-acids having arginine as the terminal amino-acid, linked to an electroactive leaving group and of which one hydrogen of the initial amino-acid can be replaced by a protective group, these amino-acids, leaving groups and protective groups being selected from very limited lists. Because of the complexity of the coagulation phenomenon due to a reaction cascade, the presence of a solvent can interfere with the intermediate products leading to a release of thrombin and thus prejudicing the accuracy of the measurement.

In an international PCT Patent Application entitled <<Oligopeptidderivative>> filed on the same day by the company Pentapharm AG (Basel, Switzerland), a particular selection of the constituent links of the substrate, in particular of the amino-acids and leaving group, allow determination of the coagulation time of a blood sample in a liquid medium to be performed, using a measuring cell of the same type as used previously, without it being necessary to add a solvent or a co-solvent to keep the substrate in solution. Even if the use of these new substrates has a certain advantage, the use of a measuring cell, with the handling which this requires, still does not provide a patient, who would like to check his coagulation time himself, with an apparatus which is easy to transport and simple to use.

SUMMARY OF THE INVENTION

The object of the system according to the invention is to overcome the drawbacks which still exist in the systems of the prior art by providing an apparatus and sensors of much smaller size as a result of the use of specific reagents and a different methodology to that previously used for determining an individual coagulation time.

The invention thus concerns an electrochemical system for measuring a value representing the coagulation time of a drop of whole blood characterised in that it includes:

an electrochemical sensor in the shape of a strip of small dimensions bearing at least a reference electrode and a working electrode on which a specific reagent is immobilised, the composition of said reagent incorporating at least one chemical substrate one terminal link of which can be cut off by the thrombin enzyme to give charged groups (LG), and a measuring apparatus whose electronic circuit, which is supplied with power by a power source, allowing a variable or non variable electric current or a variable or non variable potential difference to be imposed across the electrodes of the sensor, the electric signal resulting from the migration of the charged groups to be processed, said signal to be correlated with a value representing the coagulation time, and said value to be displayed on a display panel of said measuring apparatus.

The specific reagent immobilised on the working electrode further includes a thromboplastin and a buffer medium.

The chemical substrate one terminal link of which can be cut off by the thrombin enzyme to release charged groups LG must have a stereospecific site for the thrombin enzyme. An appropriate chemical substrate is for example formed by an oligopeptidic derivative and more particularly an oligopeptidic derivative having arginine (arg) as the terminal amino-acid linked to a group able to be cut off by thrombin to give charged groups (LG). According to a preferred embodiment, these groups which can be released by thrombin are selected from the amino-aryl or amino-heteroaryl groups which may be substituted, the link with arginine being performed by one of their amine functions.

BRIEF DESCRIPTION OF THE DRAWINGS

The invention will be explained in more detail with reference to the annexed drawings, in which.

DETAILED DESCRIPTION OF THE INVENTION

Figure 1:
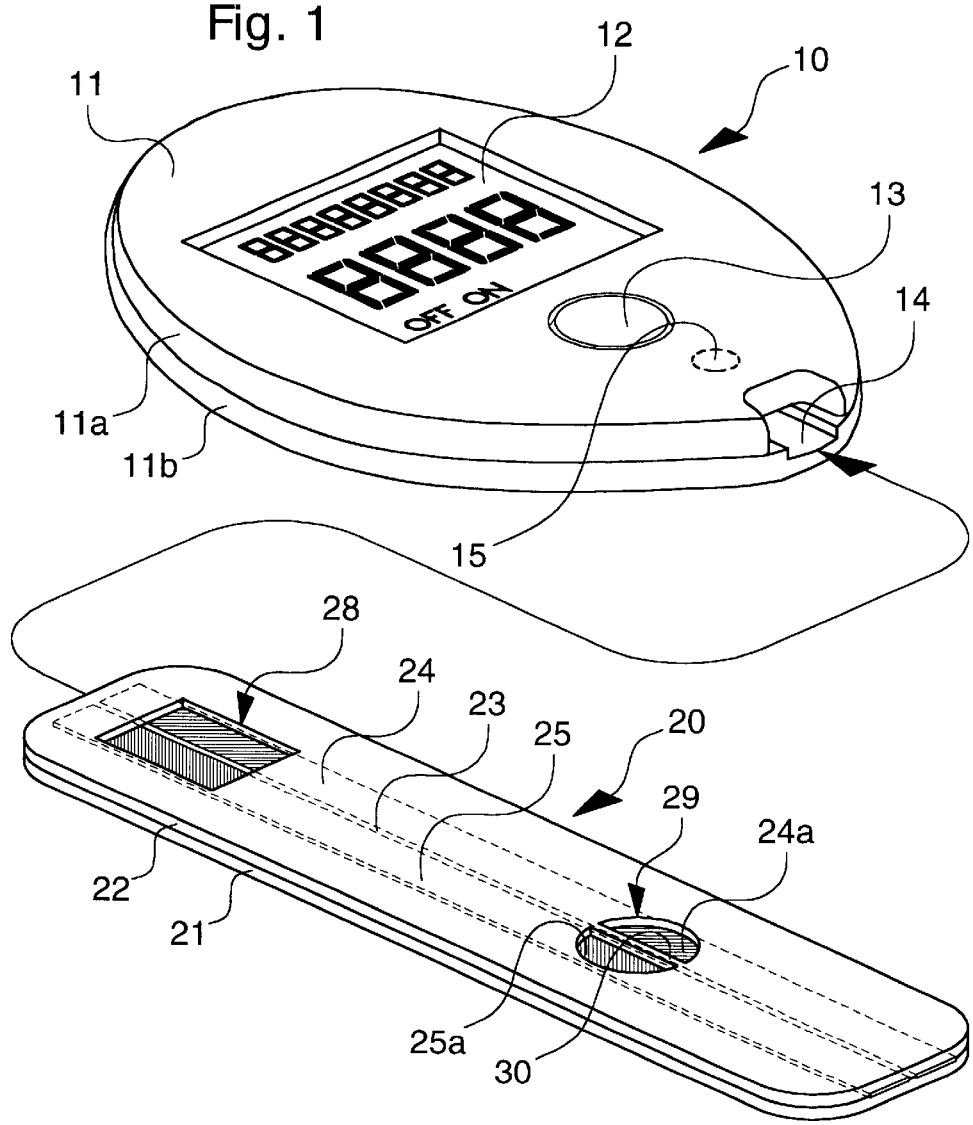
FIG. 1 shows in perspective a measuring apparatus and a sensor for a system according to the invention for determining blood coagulation time.

FIG. 1 shows substantially on a scale of 1:1, a measuring apparatus 10, and substantially on a scale of 3:1, an electrochemical sensor 20 in the shape of a strip approximately 40 mm long and 8 mm wide.

The unit formed by the apparatus and a pack of several sensors thus has a bulk comparable to that of any other portable apparatus, which allows a patient to carry it on his person as he moves around.

Measuring apparatus 10 and electrochemical sensor 20 originate from the same technology comparable to that used for the quantitative analysis of glucose levels, for example by an amperometric method as disclosed in U.S. Pat. Nos. 5,378,628, 5,532,602 and European Patent No. EP 0 787 984.

Measuring apparatus 10, as such, includes a case 11 of ovoid shape in the example shown, constructed by assembling two moulded plastic elements 11a, and 11b, of which the top element 11a includes a window for a display panel 12, and an opening for a control button 13 allowing access to the various display modes.

The electronic circuit included in the case is an adaptation of the circuits used for glucose analysis, for example by amperometry as indicated previously, and differs only therefrom in the different electric signal parameters in order to display a coagulation time.

Measuring apparatus 10 also includes a slit 14, arranged substantially between the two portions 11a, 11b of case 11, into which a portion of sensor 20 including a contact zone 28 is introduced. The other portion of sensor 20 including a measuring zone 29 intended to receive a blood sample, will remain outside apparatus 10 during the entire measuring time. In most of the measuring apparatuses of the prior art, the sample is introduced inside the apparatus into an enclosure generally thermoregulated at 37° C., which leads to additional power consumption.

In the system according to the invention, in which the sample is not introduced into a thermoregulated enclosure, it is easy to provide, if necessary a heat probe 15 on the apparatus in proximity to slit 14 to adjust the electric signal parameters as a function of the ambient temperature, with a much lower power consumption than that necessary to thermoregulate an enclosure.

Electrochemical sensor 20 shown in FIG. 1 is of the type of those used for determining glucose levels by amperometry as indicated previously. It includes a thin plastic support 21, made for example of PET, supporting over its entire length two current collectors 24, 25 separated by a small space 23 which insulates them electrically.

Support 21 and collectors 24, 25 are coated with an insulating coating 22 into which two windows 28, 29 are cut, close to each end, for example by stamping, allowing portions of collectors 24, 25 to appear. A first window 28 allows sensor 20 to be electrically connected to measuring apparatus 10, while second window 29 constitutes the measuring zone, the visible collector portions respectively forming the working electrode 24a and the reference electrode 25a.

Working electrode 24a is for example made by laminating a thin strip of platinum and reference electrode 25a by laminating a thin strip of subsequently chlorinated silver to form at the same time a reference electrode. It is also possible to provide separately, in measuring zone 29, a working electrode, a reference electrode and a counter electrode. The working electrode is coated with a specific reagent 30 described in more detail hereinafter to allow the prothrombin time (PT) to be measured.

The specific reagent is immobilised in dry form from a composition including in the example described here at least one tromboplastin, a buffer medium and an oligopeptidic substrate having a stereospecific configuration of a site of the thrombin enzyme to allowing cutting off of a charged terminal portion generally designated the <<leaving group>> (LG). In the experiments reported hereinafter, the substrate used is characterised in that the oligopeptidic derivative or one of its salts includes in addition to arginine at least one other radical amino-acid selected from among 2-aminobutyric acid (Abu), alanine (Ala), 3-cychlohexylalanine (Cha), 2-cyclohexylglycine (Chg), phenylalanine (Phe), pipecolic acid (Pip), proline (Pro), valine (Val) and glycine (Gly) said amino-acids being able to be in the L, D or DL form.

These oligopeptides and the manner in which they are obtained are described in more detail in the aforecited Patent Application by the company Pentapharm AG, and in which the great advantage of these oligopeptides for determining a coagulation time has been established by experiment in a liquid medium by means of a laboratory cell. It is thus specified that the present invention does not concern said oligopeptides as such, but the conditions for optimising compositions which, when they are deposited in dry form on an electrochemical sensor, allow an electric signal to be obtained which is sufficient to be processed, which allows good linearisation and whose response time is sufficiently short.

Likewise the leaving group (LG) which, in the conditions of the invention, must both react easily with the acid function of arginine (Arg), be able to be cut off by thrombin and have a sufficient charge, is preferably selected from among aniline, quinolylamine and naphtylamine derivatives possibly substituted by one or more substituents selected from among an halogen, an hydroxy, amino, nitro, alkyl, alkoxy, alkanoyl, anilino and aminophenyl radical, which may be substituted.

Experiments have shown that a given substrate can allow an electric signal to be detected in a liquid medium, while being inoperative or inefficient when the same substrate is used in a dry form deposited on the working electrode of an electrochemical sensor. One of the factors which may explain this difference is the fact that the oligopeptide must be immobilised on the working electrode via the opposite end of its chain to that including the leaving group LG. This result can be achieved by the first amino-acid of the oligopeptic chain, but preferably a hydrogen of its terminal amino function is replaced by a protective group R, selected from among the Boc (terbutoxycarbonyl), Tos (paratoluenesulfonic), t-Bups (ter-butylphenylsulfonyl), Mes (methylsulfonyl), Naps (2-naphtylsulfonyl), Bzo (benzoyl), Z (benzyloxycarbonyl), isopropylsulfonyl, camphosulfonyl acids.

According to a preferred embodiment, the protective group, the α-amino-acids and their chain formation, as well as the leaving group are selected so as to have the following oligopeptidic substrates:

Z-Gly-Pro-Arg-3-chloro-4-hydroxyanilide
Tos-Gly-Pro-Arg-3-chloro-4-hydroxyanilide
Boc-(D)-Chg-Gly-Arg-3-chloro-4-hydroxyanilide
H-(D)-Chg-Gly-Arg-3-chloro-4-hydroxyanilide
Z-Gly-Pro-Arg-2- chloro-4-hydroxyanilide
and their compatible mineral or organic salts.

The oligopeptides in the composition of the specific reagent are generally used in the form of one of their salts, formed for example with hydrochloric acid (HCl), acetic acid or trifluoroacetic acid (TFA).

All the reagents allowing a coagulation time to be determined, such as the prothrombin time, contain a tromboplastin in their composition. In the most recent analysis methods reconstituted thromboplastin is used in order to avoid the drawbacks of substances extracted from living tissues, such as the risk of contamination and interference with medicines or their metabolites carried by the blood. This concerns for example the product Innovin® (Dade Int. Ill. USA) which forms in particular the subject of European Patent No. EP 0 565 665, the composition of which includes 25 to 35% negative polarity phosphatidlyserine (PS) and 65 to 75% positive polarity phosphatidlyserine (PS).

Surprisingly, it was observed that the system according to the invention allowed better determination (signal height, linearity) of the prothrombin time (PT) to be obtained conversely using a tissue factor with phospholipids having a reverse PS/PC ratio, in which the quantity of negative phospholipids is greater than the quantity of positive phospholipids.

The specific reagent can incorporate in its composition as activator a calcium salt such as $CaCl_2$. However, the optimising conditions obtained mean that it is not always necessary to incorporate a calcium salt given that the concentration of $Ca^{++}$ in the whole blood is already sufficient for activation.

As in most biological reactions, it is necessary to keep the medium at a determined pH and to have sufficient ionic force. Among all the buffer mediums well known to those skilled in the art, the Hepes buffer (sulphonic N-2-hydroxyethylpiperazin-N'2-aminoethan acid) is the one which has proved most appropriate when oligopeptide substrates of the Pentapharm company are used, as will be shown hereinafter.

It will be observed finally that the immobilisation of the specific reagent on the working electrode from a liquid or consistent composition may be obtained, without other additives, by techniques known to those skilled in the art. The lyophilisation technique has however proved the most satisfactory, as will be shown hereinafter.

Figure 2:
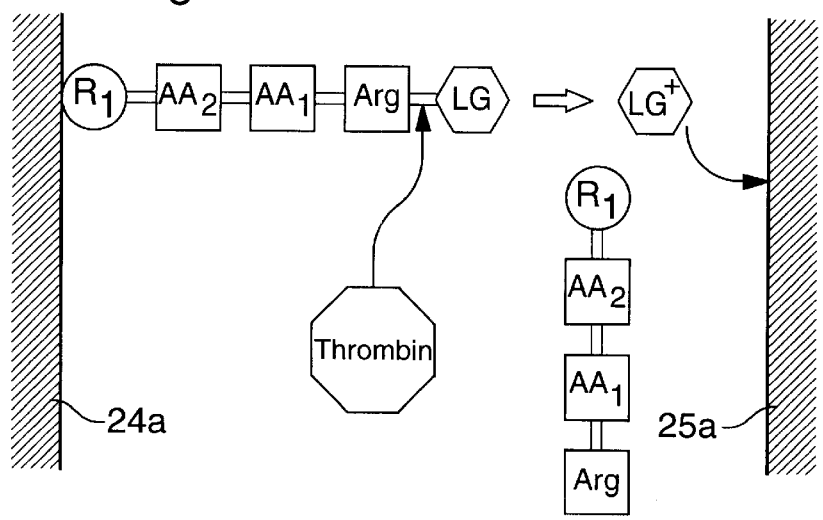
FIG. 2 is a diagram of the process leading to an electric signal which can be exploited by the measuring apparatus.

FIG. 2 is a schematic diagram of the chemical reaction which allows a current to be generated across electrodes 24a and 25a which are connected by an electronic detection circuit which is not shown. The substrate, which can be schematically represented by the formula $R1-AA_2-AA_1-Arg-LG$ in which $AA_1$ and $AA_2$ represent other amino-acids as previously indicated, is connected to working electrode 24a by the group R1 which orients the oligopeptide, and the other end of whose chain includes a leaving group LG as defined previously. In the left part of the diagram, it is seen that the thrombin enzyme selectively cuts off the connection between the arginine and said leaving group LG. In the right part of the diagram, it is seen that the leaving group released can migrate towards electrode 25a and generate a current which will be proportional to the number of leaving groups LG released, and thus to the quantity of thrombin formed in the sample.

The experiments reported hereinafter also show that the oligopeptide substrates used are selectively cut off by the thrombin enzyme to the exclusion of all other enzymes present in whole blood.

In the experiments reported hereinafter, potentiostatic measurements were performed by chronoamperometry by means of a potentiostat PGP 201 connected to the $Vm_1$ software of Radiometer (Copenhagen) allowing the following conditions to be obtained:

| | |
|---|---|
| Potential 1: 0 mV | Time 1: 1 sec. |
| Potential 2: 300 mV | Time 2: 5 min. |
| Number of cycles: 1 | Measuring frequency: 1/sec. |
| Minimum current: −50 mA | Maximum current: 50 mA |
| Minimum sensitivity: 1 µA | |

The surface of the working electrode of the sensor used is 0.035 cm² and the sample quantity, drop of blood, or reference solution is 10 µl. the recording of measurements starts 10 seconds after the sample is deposited. The oligopeptide used, hereinafter designated according to use by <<substrate>>, selected from those indicated previously, is: Tos-Gly-Pro-Arg-3-chloro-4-hydroxyanilide, 2HCl.

EXPERIMENT 1

Influence of the PC/PS Ratio

It is known that the reconstituted human tissue factor activated by a phosphatidylserin (PS) and a phosphatidylcholin (PC) in a proportion 30/70 activates coagulation in the plasma in the presence of $Cacl_2$. This composition also allows activation in whole blood, but the search for optimisation has proved necessary in order to obtain a sufficiently high amperometric signal. In order to do this series of measurements have been performed varying the PS/PC ratio, as indicated hereinafter.

In 1000 µl of a solution of <<TRIS buffer>> (trimethylol aminoethane 50 nM, NaCl/100M, $NaN_3$, 0.02%) containing 2.5 mg of deoxycholic acid sodium salt 5 µMol of PC was dissolved using an ultrasound bath for 5 minutes to obtain a first original solution. Likewise a second original solution was prepared containing 5 µMol of PS. The two original solutions were then mixed to obtain a total phospholipid concentration (PS+PC) of 2.5 mg per 1000 µl, after adjustment with the aforecited dilution solution, so as to have the following range:

| |
|---|
| a - PC 100%–PS 0% |
| b - PC 75%–PS 25% |
| c - PC 50%–PS 50% |
| d - PC 25%–PS 75% |
| e - PC 0%–PS 100% | said percentages being expressed in mol %.

10 µl of tissue factor in a concentration of 164 mg/ml (Recombinant human tissue factor from American Diagnostica 4500) was also mixed with 20 µl of distilled water, then 10 µl of a preceding PS/PC composition was added, topped up to 600 µl with a TRIS solution containing BSA (Bovine Serum Albumin) at the rate of 1 mg/ml of BSA per 260 µl, which is then agitated for 2 minutes. 220 µl of this solution is then diluted with TRIS solution until a final volume of 1100 µl is obtained. The preceding operation is repeated with the other PS/PC compositions so as to have a range of 5 different thromboplastin solutions.

Finally, by using an ultrasound bath for 5 minutes, the substrate is dissolved in each of the preceding solutions at a concentration of 0.33 mg/ml (0.5M/l), so as to obtain 5 substrate solutions, i.e. 5 specific reagents in which the PC/PS ratio varies in the previously indicated proportions.

The electrochemical sensors subjected to the experiment are finally prepared by depositing 10 µl of specific reagent on the working electrode, then by drying in an oven at 30° for 2 hours.

Figure 3A:
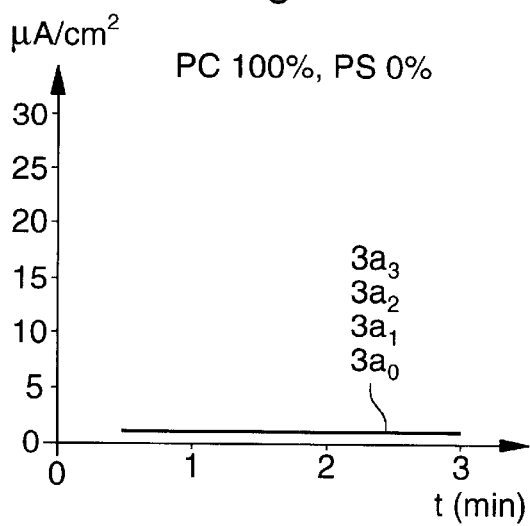
FIGS. 3a to 3e show signal variation curves as a function of the PC/PS ratio.
Figure 3B:
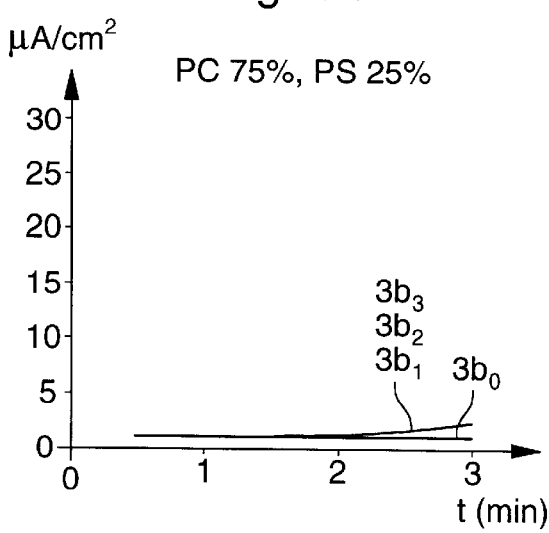
Figure 3C:
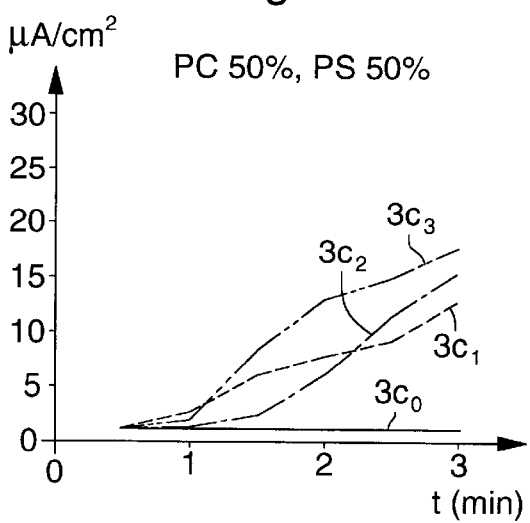
Figure 3D:
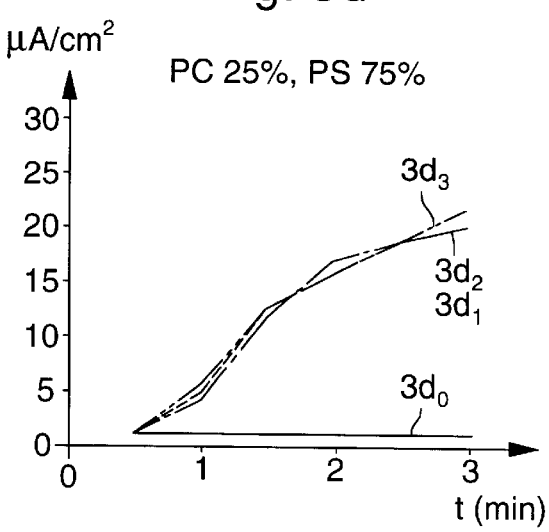
Figure 3E:
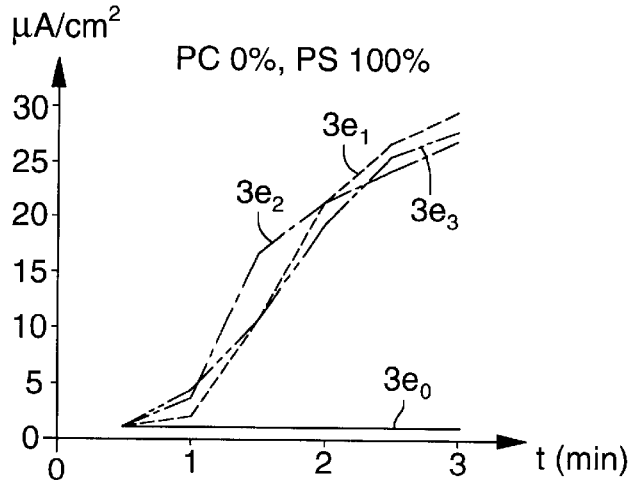

FIGS. 3a to 3e are curves representing the current density expressed in µA/cm² as a function of time expressed in minutes, the results recorded for three different tests (3a1, 3a2, 3a3; 3b1, 3b2 . . . etc.) with reference to a blank test (3a0, 3b0, 3c0, 3d0, 3e0) containing 10 µl of TRIS buffer in place of 10 µl of whole blood. As is seen in FIG. 3a, curves 3a0, 3a1, 3a2 and 3a3 are identical, i.e. no electric signal is obtained when the PC/PS ratio is 100/0. When the PC/PS ratio is 75/25, which corresponds to the preferred ratio of the composition Innovin®, FIG. 3b shows that the current density is very low and is scarcely different from the blank test curve 3b0. When PC and PS are in equal quantities (FIG. 3c) one obtains a significative current density but too great a dispersion of measurements. With a PC/PS ratio of 25/75 it is seen in FIG. 3d that curves 3d1, 3d2, 3d3 are practically identical, i.e. one obtains good reproducibility and satisfactory linearity. By using PS alone (FIG. 3d) the signal is higher, but the reproducibility may seem less satisfactory. These experiments show that the preferred composition must have 65% to 100% of phosphatidylserin (PS).

Moreover it will be observed that the above results were obtained without it being necessary to add $CaCl_2$, given that the concentration in calcium ion in whole blood proved sufficient.

Other experiments showed that the addition of phosphatidylethanolamine (PE) did not bring any improvement to the measurements, and that it was not possible to obtain activation solely with the tissue factor, i.e. without phospholipids.

EXPERIMENT 2

Influence of the Buffer Medium

Figure 4:
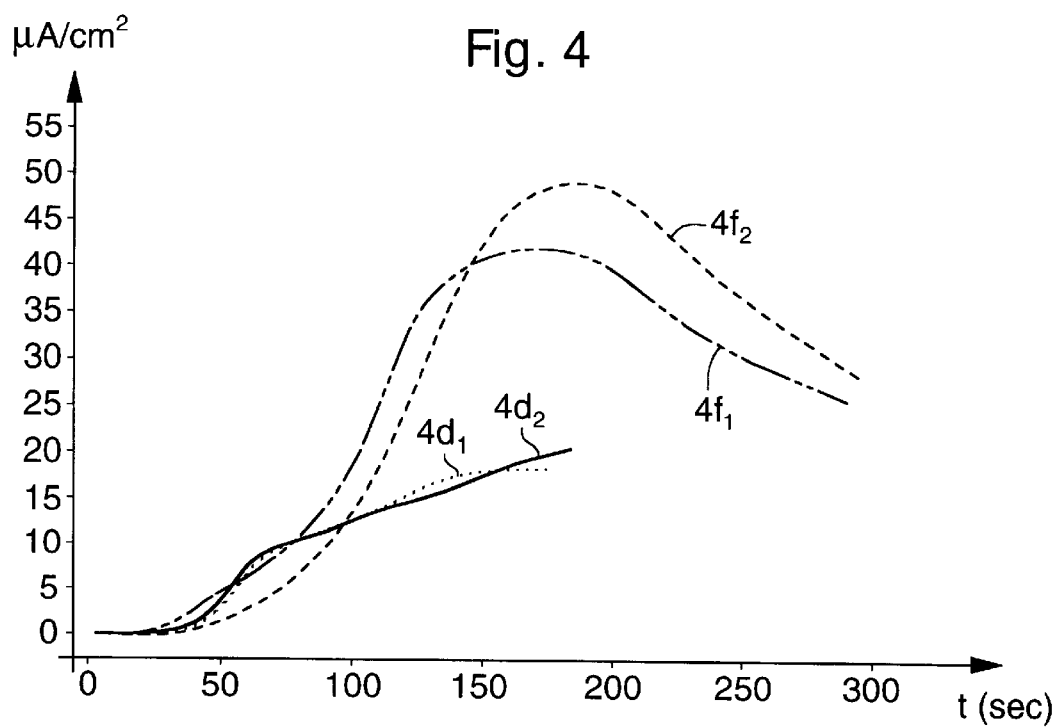
FIG. 4 shows signal variation curves as a function of the buffer medium.
Figure 5:
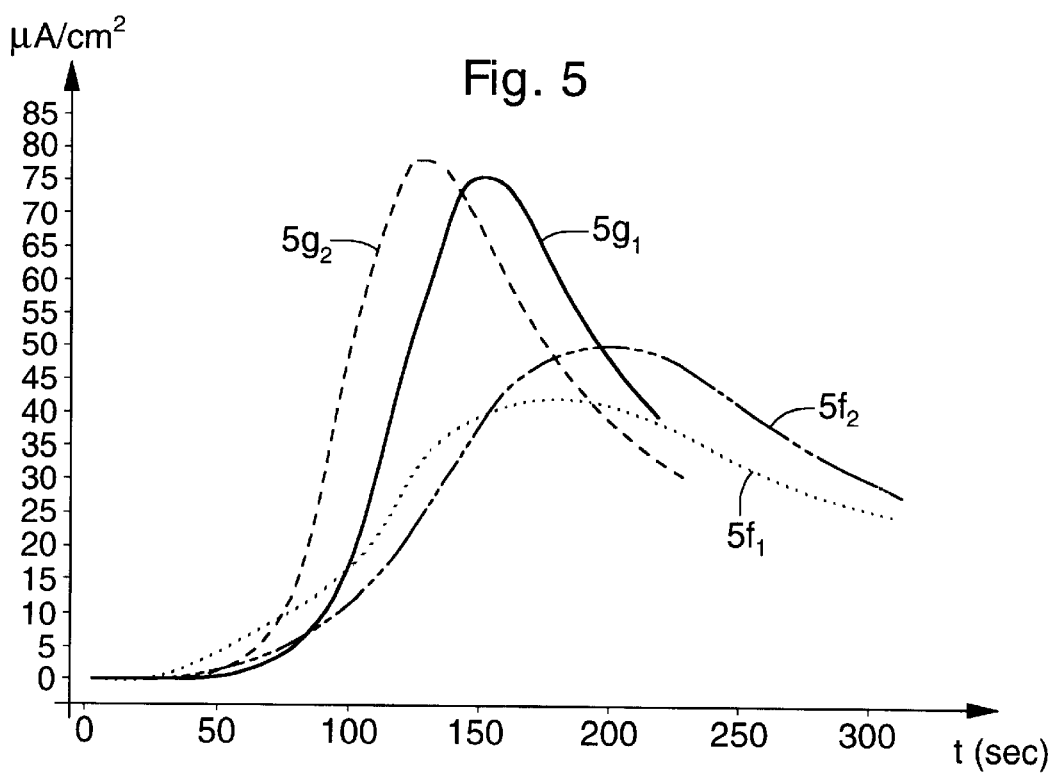
FIG. 5 shows signal variation curves as a function of the drying mode.

According to the same process as that described for experiment 1, a first substrate solution (d) was prepared containing PC-PS in the ratio 25/75 with TRIS buffer as the buffer medium, and a second substrate solution (f) in which the TRIS buffer is replaced by Hepes buffer, then two measurements were performed, corresponding respectively to curves 4d1, 4d2 (TRIS) and 4f1, 4f2 (Hepes) of FIG. 4, with each substrate solution, using a blood sample from the same patient. As is seen, a much higher signal is obtained with the Hepes buffer, which can thus be retained as the preferred buffer medium.

EXPERIMENT 3

Influence of the Drying Mode

In the present experiment, the shape of the signal obtained when the specific reagent is dried by lyophilisation was compared to that obtained by drying in an oven at 30° C. for 2 hours, as was the case in the preceding experiments. The specific reagent is the same as that of example 2 with the Hepes buffer. By using one or other drying mode, each time two measurements are effected corresponding respectively to curves 5f1, 5f2 (oven drying) and 5g1, 5g2 (lyophilisation). It can be observed that the lyophilisation technique allows a higher signal to be obtained, in a much shorter time. This can be explained by the fact that lyophilisation allows more homogeneous covering of the surface of the electrodes to be obtained than that obtained with oven drying.

Other experiments performed solely with the substrate in a buffer medium using additives which allowed the signal to be optimised in the case of a glucose sensor, showed that the use of a carbon powder to increase the specific surface had no favourable effect, because the base current due to the carbon powder interfered with the current to be measured.

EXPERIMENT 4

Specificity of the Specific Reagent vis-à-vis the Thrombin Enzyme

Figure 6:
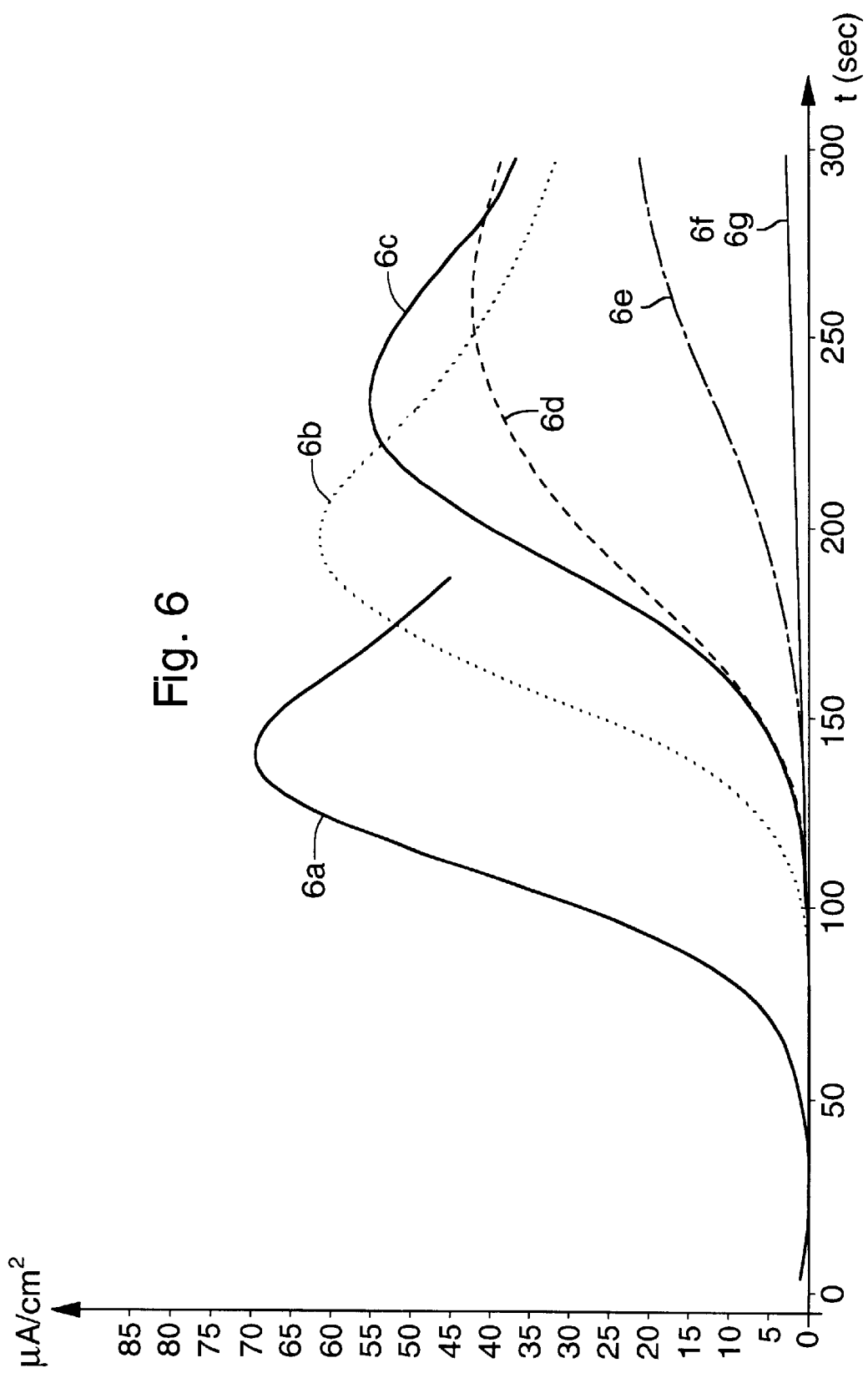
FIG. 6 shows curves showing the substrate specificity.

Given that whole blood contains extremely numerous constituents, the present experiment allows it to be shown that only the thrombin enzyme is capable of cutting the specific reagent substrate. The experiment is performed in the optimisation conditions defined by experiment 3 (namely PC/PS in the ratio 25/75, Hepes buffer and lyophilisation) starting with a dilution in equal parts of blood and buffer solution and progressively inhibiting the thrombin enzyme by increasing concentrations of r-hirudin (r-hirudin 2000 ATU/bulb, available from Pentapharm AG, Basel, Switzerland) which replace the buffer solution, preferably having checked that the factor Xa is not inhibited by r-hirudin. In FIG. 6, curve 6a is a control curve without r-hirudin and curves 6b to 6g are the curves of the measurements effected with respectively 12.5 ARU/ml; 25 ATU/ml; 37.5 ATU/ml; 50 ATU/ml; 100 ATU/ml; 1000 ATU/ml.

As is seen the height of the signal decreases gradually as the concentration in r-hirudin increases until it becomes practically zero from 100 ATU/ml. It can thus be concluded that the system according to the invention allows the substrate to be selectively cut off by thrombin, and thus to allow selective determination of this enzyme.

As is seen with reference more particularly to curves 6a, 6b and 6c, the maximum value is substantially proportional to the reduction of thrombin enzyme in the sample, which allows linear parameters relation to be envisaged. In practice, the maximum value is not taken, but the value corresponding to the change of direction point of the rising part of the curve, i.e. the point at which the speed of release of thrombin is maximum. In practice, detection windows of 15 seconds are used and one retains the value comprised between two detection windows for which the passage from an increase of the direction of the gradient to a reduction in the direction of the gradient is observed.

What is claimed is:

1. An electrochemical system for measuring a value representing the coagulation time of a drop of whole blood wherein said system includes:

an electrochemical sensor in the shape of a strip bearing at least a reference electrode and a working electrode on which a specific reagent is immobilised on a measuring zone, the composition of said reagent incorporating at least a thromboplastin having a quantity of negative phospholipids greater than that of positive phospholipids, a buffer medium and an oligopeptidic substrate, one terminal link of which can be cut off by the thrombin enzyme to give charged groups (LG), and a portable measuring apparatus dimensionally configured to receive the sensor and having an electronic circuit, which is supplied with power by a power source, allowing a variable or non variable electric current or a variable or non variable potential difference to be imposed across the electrodes of the sensor, said measuring apparatus having means for processing the electric signal resulting from the migration of the charged groups (LG), means for correlating said signal with a value representative of the coagulation time, and means for displaying said value on a display device of said measuring apparatus.

2. The measuring system according to claim 1, wherein the oligopeptidic substrate is a tripeptide having, as terminal amino-acid, arginine (Arg) linked to an amine function of a substituted amino-aryl group, said group being able to be cut off by thrombin to give the charged groups (LG).

3. The measuring system according to claim 2, wherein other amino acids of the tripeptide are selected from the group consisting of 2-aminobutyric acid (Abu), alanine (Ala), 3-cychlohexylalanine (Cha), 2-cyclohexylglycine (Chg), phenylalanine (Phe), pipecolic acid (Pip), proline (Pro), valine (Val) and glycine (Gly), said amino-acids being able to be in the L, D or DL form.

4. The measuring system according to claim 2, wherein the amino-aryl group (LG) of the oligopeptidic substrate is selected from the group consisting of aniline and quinolylamine derivatives substituted by one or more substituents selected from the group consisting of an halogen, an hydroxy, amino, nitro, alkyl, alkoxy, alkanoyl, anilino and aminophenyl radical.

5. The measuring system according to claim 2, wherein the first amino-acid of the oligopeptidic substrate further has a hydrogen of its amino function replaced by a protective group selected from the group consisting of Boc (terbutoxycarbonyl), Tos (paratoluenesulfonic), t-Bups (terbutylphenylsulfonyl), Mes (methylsulfonyl), Naps (2-naphtylsulfonyl), Bzo (benzoyl), Z (benzyloxycarbonyl), isopropylsulfonyl and camphosulfonyl acids.

6. The measuring system according to claim 5, wherein the oligopeptidic substrate is selected from the group consisting of:

Z-Gly-Pro-Arg-3-chloro-4-hydroxyanilide

Tos-Gly-Pro-Arg-3-chloro-4-hydroxyanilide

Boc-(D)-Chg-Gly-Arg-3-chloro-4-hydroxyanilide

H-(D)-Chg-Gly-Arg-3-chloro-4-hydroxyanilide

Z-Gly-Pro-Arg-2-chloro-4-hydroxyanilide and compatible mineral or organic salts of said oligopeptidic substrate.

7. The measuring system according to claim 6, wherein an oligopeptidic substrate salt is formed with hydrochloric acid (HCl), acetic acid or trifluoroacetic acid (TFA).

8. The measuring system according to claim 1, wherein the level of the negative phospholipids is greater than 65%.

9. The measuring system according to claim 1, wherein the specific reagent of the sensor further includes in its composition a calcium salt such as $CaCl_2$.

10. The measuring system according to claim 1, wherein the buffer of the specific reagent of the sensor is the HEPES buffer.

11. The measuring system according to claim 1, wherein the specific reagent of the sensor is first prepared in liquid or pasty form, applied onto the working electrode with a pipette or by silk screen process, and then brought to the dry state by lyophilisation.

12. The measuring system according to claim 1, wherein the power source of the portable measuring apparatus is an autonomous power source including a battery.

13. The measuring system according to claim 1, wherein the portable measuring apparatus further includes means for bringing the measuring zone to a determined temperature and keeping it at that temperature.

14. An electrochemical system for measuring a value representing the coagulation time of a drop of whole blood wherein said system includes:

an electrochemical sensor in the shape of a strip bearing at least a reference electrode and a working electrode on which a specific reagent is immobilised, the composition of said reagent incorporating at least one chemical substrate, one terminal link of which can be cut off by the thrombin enzyme to give charged groups (LG), and a measuring apparatus dimensionally configured to receive the sensor and whose electronic circuit, which is supplied with power by a power source, allowing a variable or non variable electric current or a variable or non variable potential difference to be imposed across the electrodes of the sensor, said measuring apparatus having means for processing the electric signal resulting from the migration of the charged groups (LG), means for correlating said signal with a value representative of the coagulation time, and means for displaying said value on a display device of said measuring apparatus;

wherein the chemical substrate of the specific reagent is an oligopeptidic derivative;

wherein the oligopeptidic derivative has, as terminal amino-acid, arginine (Arg) linked to an amine function of a substituted amino-aryl group, said group being able to be cut off by thrombin to give the charged groups (LG); and wherein the oligopeptidic substrate is selected from the group consisting of:

Z-Gly-Pro-Arg-3-chloro-4-hydroxyanilide

Tos-Gly-Pro-Arg-3-chloro-4-hydroxyanilide

Boc-(D)-Chg-Gly-Arg-3-chloro-4-hydroxyanilide

H-(D)-Chg-Gly-Arg-3-chloro-4-hydroxyanilide

Z-Gly-Pro-Arg-2-chloro-4-hydroxyanilide and compatible mineral or organic salts of said oligopeptidic substrate.

15. The measuring system according to claim 14, wherein an oligopeptidic substrate salt is formed with hydrochloric acid (HCl), acetic acid or trifluoroacetic acid (TFA).

* * * * *